(12) United States Patent
Yokozawa et al.

(10) Patent No.: US 6,333,291 B1
(45) Date of Patent: Dec. 25, 2001

(54) OPTICALLY ACTIVE DIPHOSPHINE COMPOUND, PRODUCTION INTERMEDIATE THEREOF, TRANSITION METAL COMPLEX CONTAINING THE COMPOUND AS LIGAND AND ASYMMETRIC HYDROGENATION CATALYST CONTAINING THE COMPLEX

(75) Inventors: Tohru Yokozawa; Noboru Sayo; Takao Saito; Takero Ishizaki, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/698,208

(22) Filed: Oct. 30, 2000

(30) Foreign Application Priority Data

Oct. 29, 1999 (JP) .................................................. 11-309976

(51) Int. Cl.$^7$ ............................... B01J 31/00; C07F 9/50; C07F 9/53; C07F 15/00
(52) U.S. Cl. ............................ 502/162; 568/14; 568/17; 549/218; 556/13; 556/21
(58) Field of Search .................................. 568/8, 13, 14, 568/15, 17; 549/218; 556/21, 13; 502/162

(56) References Cited

FOREIGN PATENT DOCUMENTS 1 002 801 A1    5/2000  (EP) .

OTHER PUBLICATIONS

CA:133:309942 abs of J Org. Chem. by Z Zhang et al 65(19) pp 6223–6226, Sep. 2000.*
CA:133:4801 abs of EP1002801, May 2000.*
O. M. Petrukhin, et al., "Potentiometric Selectivity of Ion-selective Electrodes for Alkaline–Earth Elements based on podands with phosphoryl terminal groups", Anal. Chim. Acta (1997), 353(1), pp. 11–27.

R. Schmid et al., "New Developments in Enantioselective Hydrogenation" Pure & Applied Chemistry, GB, Pergamon Press, Oxford, vol. 68, No. 1, 1996, pp. 131–138.

Schmid et al, "102. Axially Dissymmetric Bis(triaryl) phosphines in the Biphenyl Series: Synthesis of (6,6'–Dimethylibhenyl–2,2'–diyl)bis(diphenylphosphine) ('BIPHEMP)') and Analogues, and their Use in Rh(I)–Catalyzed Asymmetric Isomerizations of N,N–Diethylnerylamine", Helvetica Chimica Acta, vol. 71 (1998), pp. 896–929.

* cited by examiner

*Primary Examiner*—Jean F. Vollano
(74) *Attorney, Agent, or Firm*—Sughrue, Mion, Zinn, Macpeak & Seas, PLLC

(57) ABSTRACT

This invention provides a novel diphosphine compound which is useful as a ligand of catalysts for asymmetric synthesis reactions, particularly asymmetric hydrogenation reaction. Particularly, it provides a diphosphine compound represented by a general formula (1):

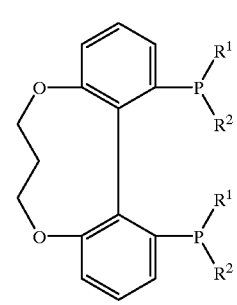

(1)

wherein $R^1$ and $R^2$ each independently represents a cycloalkyl group, an unsubstituted or substituted phenyl group or a five-membered aromatic heterocycle residue.

7 Claims, No Drawings

OPTICALLY ACTIVE DIPHOSPHINE COMPOUND, PRODUCTION INTERMEDIATE THEREOF, TRANSITION METAL COMPLEX CONTAINING THE COMPOUND AS LIGAND AND ASYMMETRIC HYDROGENATION CATALYST CONTAINING THE COMPLEX

FIELD OF THE INVENTION

This invention relates to a novel optically active diphosphine compound, a production intermediate thereof, a transition metal complex containing the diphosphine compound as a ligand and a transition metal complex catalyst useful as a catalyst of various asymmetric synthesis reactions.

BACKGROUND OF THE INVENTION

A large number of transition metal complexes have been reported, which can be used in asymmetric syntheses such as asymmetric hydrogenation reaction, asymmetric isomerization reaction and asymmetric hydrosilylation reaction. Particularly, a complex in which an optically active tertiary phosphine compound is coordinated to a transition metal complex such as of ruthenium, rhodium, iridium or palladium has excellent performance as a catalyst of asymmetric synthesis reactions.

In order to further improve this performance, a large number of phosphine compounds having various structures have so far been developed (Chemical Review 32 "Chemistry of Organic Metal Complex", pp. 237–238, 1982, edited by The Chemical Society of Japan; "Asymmetric Catalysis In Organic Synthesis", edited by R. Noyori, A Wiley-Interscience Publication).

Particularly, 2,2'-bis(diphenylphosphino)-1,1'-binaphthyl (to be referred to as "BINAP" hereinafter) is one of the excellent optically active phosphine compounds, and a rhodium complex (JP-A-55-61973; the term "JP-A" as used herein means an "unexamined published Japanese patent application") and a ruthenium complex (JP-A-61-63690), which contain the BINAP as a ligand, have already been reported.

Also, it has been reported that a rhodium complex (JP-A-60-199898) and a ruthenium complex (JP-A-61-63690), which contain 2,2'-bis(di-(p-tolyl)phosphino)-1,1'-binaphthyl (to be referred to as "p-TolBINAP" hereinafter) as a ligand, give good results in asymmetric hydrogenation reaction and asymmetric isomerization reaction. In addition, it has been reported in JP-A-3-255090 that a ruthenium complex of 2,2'-bis(di-(3,5-dialkylphenyl)phosphino)-1,1'-binaphthyl gives excellent results in asymmetric hydrogenation of β-ketoesters.

However, since their selectivity (chemical selectivity or enantio-selectivity) and catalytic activities are not sufficient depending on the intended reactions or reaction substrates thereof, there are cases in which these catalysts have to be improved.

SUMMARY OF THE INVENTION

In view of the above, it therefore becomes an object of the invention to provide a novel catalyst which has excellent performance (chemical selectivity, enantio-selectivity and catalytic activity) as a catalyst of asymmetric synthesis reactions, particularly asymmetric hydrogenation reaction.

The invention also contemplates providing a novel phosphine compound and further providing a novel phosphine compound which is useful as a ligand of the catalyst.

With the aim of achieving these objects, the present inventors have conducted intensive studies and found as a result of the efforts that a transition metal complex of an optically active diphosphine compound represented by the following formula (6) (to be referred sometimes to as 7,8-dihydro-6H-dibenzo[f,h][1,5]dioxonine-1,13-diyl-bis (diphenylphosphine) hereinafter) is effective as a catalyst component which is concerned in the asymmetric hydrogenation reaction, and that this transition metal complex exerts excellent catalytic activity and enantio-selectivity in the asymmetric hydrogenation reaction of benzoylacetic acid esters. Thereafter, the invention has been established by further conducting evaluations.

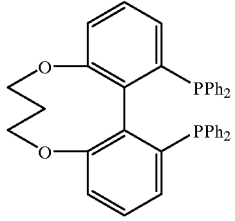

(6)

In this connection, the inventors have already developed a transition metal complex of ((5,6), (5',6')-bis-(methylenedioxy)biphenyl-2,2'-diyl)bis (diphenylphosphine) (to be referred to as "SEGPHOS" hereinafter), but effects of the transition metal complex of diphenylphosphine compound of the invention are equal to or higher than those of the above transition metal complex.

Other objects and advantages of the invention will be made apparent as the description progresses.

DETAILED DESCRIPTION OF THE INVENTION

One of the diphosphine compounds of the invention is a compound represented by the following general formula (1):

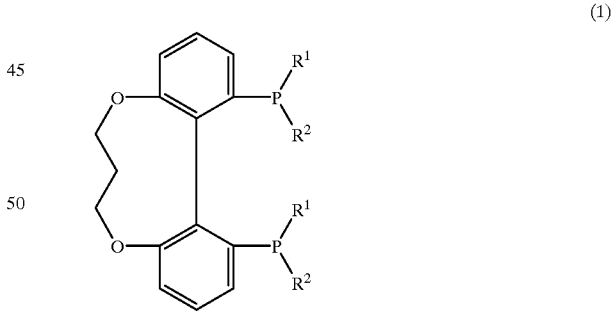

(1)

wherein $R^1$ and $R^2$ each independently represents a cycloalkyl group, an unsubstituted or substituted phenyl group or a five-membered aromatic heterocycle residue.

The cycloalkyl group is preferably cyclopentyl group, cyclohexyl group or cycloheptyl group, the five-membered aromatic heterocycle residue is preferably 2-furyl group, 3-furyl group, 2-benzofuryl group or 3-benzofuryl group, and the substituent group of the substituted phenyl group is preferably an alkyl group having from 1 to 4 carbon atoms, an alkoxy group having from 1 to 4 carbon atoms, a di(lower alkyl)amino group or a halogen atom. The term "lower alkyl" as used herein means an alkyl group having from 1 to 5 carbon atoms.

Preferred among these compounds is a compound of a formula (7):

(7)

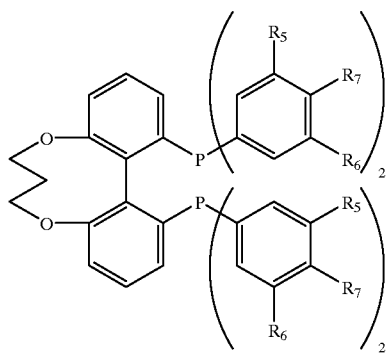

wherein $R^5$ and $R^6$ each independently represents a hydrogen atom, an alkyl group having from 1 to 4 carbon atoms or an alkoxy group having from 1 to 4 carbon atoms, and R represents a hydrogen atom, an alkyl group having from 1 to 4 carbon atoms, an alkoxyl group having from 1 to 4 carbon atoms or a di (lower alkyl)aminogroup. The term "lower alkyl" as used here in means an alkyl group having from 1 to 5 carbon atoms.

More preferred is a compound in which $R^5$ and $R^6$ are the same and selected from the group consisting of hydrogen atom, t-butyl group, n-butyl group, n-propyl group, isopropyl group, ethyl group and methyl group, and $R^7$ is selected from the group consisting of hydrogen atom, t-butoxy group, isopropoxy group, ethoxy group and methoxy group.

A diphosphine oxide compound represented by the following formula (2) is also a compound which belongs to the invention:

(2)

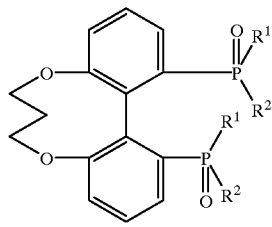

wherein $R^1$ and $R^2$ are as defined in the foregoing.

The compound of formula (2) is a production intermediate of the diphosphine compounds of formulae (1) and (7).

A compound represented by the following formula (3) is also a compound which belongs to the invention:

(3)

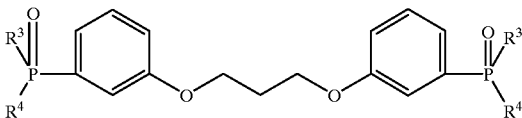

wherein $R^3$ and $R^4$ each independently represents a cycloalkyl group, an unsubstituted or substituted phenyl group, a five-membered aromatic heterocycle residue, an alkoxyl group having from 1 to 4 carbon atoms, phenoxy group, benzyloxy group, chlorine atom or bromine atom.

In this connection, the compound represented by formula (3) can be divided into a compound in which $R^3$ and $R^4$ each independently represents a cycloalkyl group, an unsubstituted or substituted phenyl group or a five-membered aromatic heterocycle residue and a compound in which $R^3$ and $R^4$ each independently represents an alkoxyl group having from 1 to 4 carbon atoms, phenoxy group, benzyloxy group, chlorine atom or bromine atom.

Of these two compounds, the former is a production intermediate of the compound of formula (2) and the latter is a production intermediate of the former compound.

In addition, racemic modifications and optically active compounds of the above compounds are also the compounds which belong to the invention.

Methods for the production of these compounds are described in the following.

For the sake of avoiding complexity, production methods of the compounds of the invention are illustratively described using an optically active (−)-form of a compound represented by the following formula (8), ((−)-7,8-dihydro-6H-dibenzo[f,h][1,5]dioxonine-1,13-diyl-bis (diphenylphosphine)), as an example of the compounds included in the invention. However, the invention is not limited to this example.

(8)

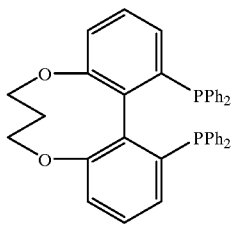

That is, 3,3'-dibromo-1,1'-trimethylenedioxydibenzene (10) is prepared by allowing sodium hydride and trimethylene dibromide to react with 3-bromophenol (11). The compound (10) is allowed to react with magnesium pieces to obtain a Grignard's reagent which is then allowed to react with diphenylphosphinyl chloride to obtain 1,1'-trimethylenedioxydibenzene-3,3'-diyl-bis (diphenylphosphine oxide) (32) ($R^1$, $R^2$=phenyl). Next, the compound (32) is made into lithium salt by allowing it to react with lithium diisopropylamide and then the salt is allowed to react with ferric chloride as an oxidizing agent to obtain a racemic compound (7,8-dihydro-6H-dibenzo[f,h][1,5]dioxonine-1,13-diyl-bis(diphenylphosphine oxide)) (2)

($R^1$, $R^2$=phenyl). Thereafter, the compound (2) is subjected to optical resolution using (−)-dibenzoyl-L-tartaric acid (to be referred to as "(−)-L-DBT" hereinafter) and then reduced using trichlorosilane, thereby obtaining ((−)-7,8-dihydro-6H-dibenzo[f,h][1,5]dioxonine-1,13-diyl-bis(diphenylphosphine)).

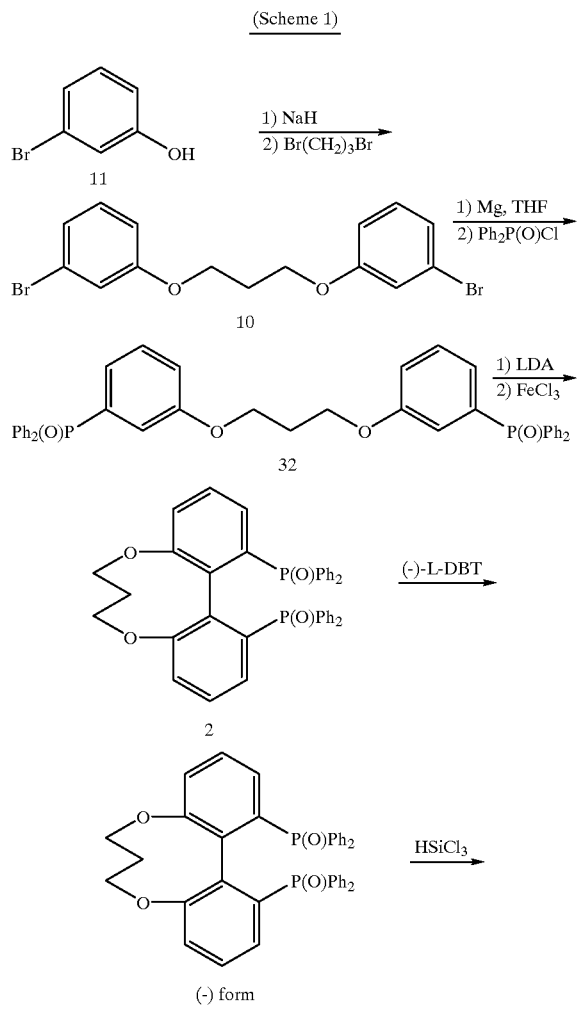

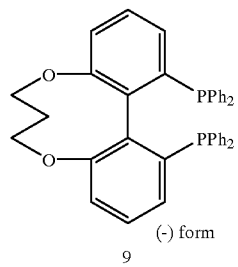

Also, an optically active (+)-form of the compound of formula (9), ((+)-7,8-dihydro-6H-dibenzo[f,h][1,5]dioxonine-1,13-diyl-bis(diphenylphosphine)), can be obtained from the compound (2) in the scheme 1 by subjecting it to optical resolution using (+)-dibenzoyl-D-tartaric acid.

In describing a preparation method of a compound which is a diphosphine compound of the above formula (1) and has a substituent group on the phenyl group, the compound of interest can be obtained by using a diphenylphosphinyl chloride derivative having a substituent group instead of diphenylphosphinyl chloride in the method of scheme 1. As an alternative method, the compound of interest can be obtained by firstly preparing a compound (31) having a substituent group on the phenyl group by the method of the following scheme 2 and then continuing the reaction using this compound (31) instead of the compound (32) of scheme 1.

Preparation of the compound (31) is carried out by allowing a compound (10) to react with magnesium pieces to obtain a Grignard's reagent which is subsequently allowed to react with diphenyl chlorophosphate to obtain a compound (4), and then allowing the compound (4) to react with a phenyl Grignard's reagent (41) having a substituent group.

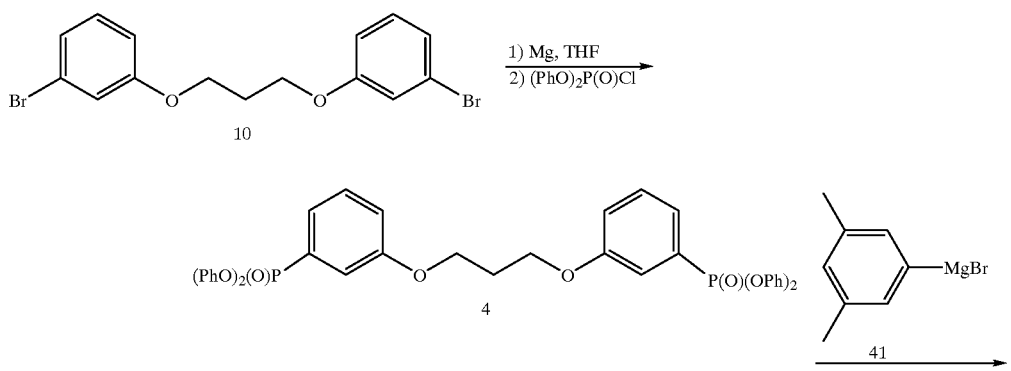

-continued

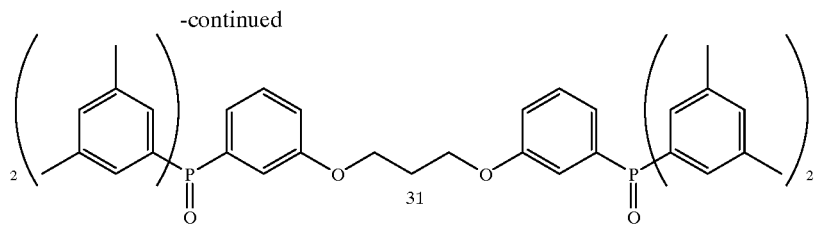

Among compounds of the invention, particularly an optically active compound of the compound (2) can also be obtained from a racemic compound of the compound (2) by carrying out optical resolution of enantiomers using an optically active column.

Among compounds of the invention, a compound (1), particularly an optically active compound thereof, is useful as a ligand of transition metal complexes. In addition, a racemic compound among compounds (1) of the invention is also useful as an intermediate for the production of optically active compounds.

The transition metal complex used in this invention includes compounds of formula (4) and compounds of formula (5):

$$M_mL_nXPS_q \quad (4)$$

wherein M represents a transition metal selected from the group consisting of rhodium, ruthenium, iridium, palladium and nickel, L represents an optically active diphosphine compound of formula (1), X is selected from the group consisting of Cl, Br, I, acetoxy group, methallyl group and π-allyl group, S represents $NEt_3$, Et represents ethyl group, m is 1 or 2, n is 1 or 2, p is 2 or 4 and q is 0 or 1, with the proviso that (i) when M=Rh, then X=Cl, Br or I, m=2, n=2, p=2, and q=0,
(ii) when M=Ru and X=acetoxy group, then m=1, n=1, p=2 and q=0,
(iii) when M=Ru and X=Cl or Br, then m=2, n=2, p=4, q=1, or
(iv) when M=Ru and X=methallyl, then m=1, n=1, p=2 and q=0,
(v) when M=Ir, then X=Cl, Br or I, m=2, n=2, p=2 and q=0,
(vi) when M=Pd and X=Cl, Br or I, then m=1, n=1, p=2 and q=0,
(vii) when M=Pd and X=π-allyl, then m=2, n=2, p=2 and q=0, and
(viii) when M=Ni, then X=Cl, Br or I, m=1, n=1, p=2 and q=o;

$$[M_mX_pL_nZ_q]Y_r \quad (5)$$

wherein M represents a transition metal selected from the group consisting of rhodium, ruthenium, iridium and palladium, L represents an optically active diphosphine compound of formula (1), X represents 1,5-cyclooctadiene, norbornadiene, Cl, Br or I, Z represents benzene or paracymene, Y represents $BF_4$, $ClO_4$, $PF_6$, $BPh_4$, Cl, Br or I and Ph represents phenyl group, m is 1, n is 1, p is 0, 1 or 2, q is 0 or 1 and r is 0, 1 or 2, with the proviso that (i) when M=Rh, then X=cod or nbd, Y=$BF_4$, $ClO_4$, $PF_6$, or $BPh_4$, m=1, n=1, p=1, r=1 and q=0,
(ii) when M=Ru and Y=Cl, Br or I, then X=Cl, Br or I=, Z=benzene or paracymene, m=1, n=1, p=1, q=1 and r=1,
(iii) when M=Ru and Y=$BF_4$, $ClO_4$, $PF_6$ or $BPh_4$, m=1, n=1, p=0, q=0 and r=2,
(iv) when M=Ir, then X=cod or nbd, Y=$BF_4$, $ClO_4$, $PF_6$ or $BPh_4$, m=1, n=1, r=1, p=1 and q=0,
(v) when M=Pd, then Y=$BF_4$, $ClO_4$, $PF_6$ or $BPh_4$, m=1, n=1, r=1, p=0 and q=0, and
(vi) when M=Ni, then X=Cl, Br or I, m=1, n=1, p=2, q=0 and r=0, wherein cod represents 1,5-cyclooctadiene and nbd represents norbornadiene.

Examples of the transition metal which forms the complex of the invention include rhodium, ruthenium, iridium, palladium and nickel.

These transition metal complexes can be produced using generally known methods.

In this connection, symbols used in the formulae of transition metal complexes shown in the following are: L, an optically active compound of the compound (1) of the invention; cod, 1,5-cyclooctadiene; nbd, norbornadiene; Ph, phenyl group; and Ac, acetyl group.

The following illustratively describes these complexes.
Rhodium complex:

An illustrative example of the method for producing a rhodium complex is a synthesis method in which bis (cycloocta-1,5-diene)rhodium(I) tetrafluoroborate and 7,8-dihydro-6H-dibenzo[f,h][1,5]dioxonine-1,13-diyl-bis (diphenylphosphine) which is the diphosphine compound of the invention are allowed to react with each other in accordance with the method described in "Jikken Kagaku Kouza, Fourth Edition", edited by The Chemical Society of Japan, Vol. 18, Organic Metal Complex, pp. 339–344, 1991, published by Maruzen Publishing. The following can be cited as illustrative examples of the rhodium complex.

[Rh(L)Cl]$_2$, [Rh(L)Br]$_2$, [Rh(L)I]$_2$,
[Rh(cod)(L)]BF$_4$, [Rh(cod)(L)]ClO$_4$,
[Rh(cod)(L)]PF$_6$, [Rh(cod)(L)]BPh$_4$,
[Rh(nbd)(L)]BF$_4$, [Rh(nbd)(L)]ClO$_4$,
[Rh(nod)(L)]PF$_6$, [Rh(nbd)(L)]BPh$_4$ Ruthenium Complex:

Regarding the method for producing a ruthenium complex, there is a preparation method described in a report (T. Ikariya, Y. Ishii, H. Kawano, T. Arai, M. Saburi, S. Yoshikawa and S. Akutagawa, *J. Chem. Soc., Chem. Commun.*, 922 (1985)), in which [Ru (cod)Cl$_2$]$_n$ (a polymer form) and 7,8-dihydro-6H-dibenzo[f,h][1,5]dioxonine-1,13-diyl-bis(diphenylphosphine) are heated under reflux in toluene solvent in the presence of triethylamine. Also, there is another preparation method described in a report (K. Mashima, K. Kusano, T. Ohta, R. Noyori and H. Takaya, *J. Chem. Soc., Chem. Commun.*, 1208 (1989)), in which [Ru (p-cymene)I$_2$]$_2$ and 7,8-dihydro-6H-dibenzo[f,h][1,5] dioxonine-1,13-diyl-bis(diphenylphosphine) are heated and stirred in methylene chloride and ethanol.

The following can be cited as illustrative examples of the ruthenium complex.

Ru(OAc)$_2$(L), Ru$_2$Cl$_4$(L)$_2$NEt$_3$,
[RuCl(benzene)(L)]Cl, [RuBr(benzene)(L)]Br,
[RuI(benzene)(L)]I,
[RuCl(p-cymene)(L)]Cl, [RuBr(p-cymene)(L)]Br,
[RuI(p-cymene)(L)]I,
[Ru(L)](BF$_4$)$_2$, [Ru(L)(ClO$_4$)$_2$, [Ru(L)(PF$_6$)$_2$,
Ru(L)](BPh$_4$)$_2$ Iridium Complex:

An iridium complex can be prepared by allowing 7,8-dihydro-6H-dibenzo[f,h][1,5]dioxonine-1,13-diyl-bis(diphenylphosphine) to react with [Ir(cod)(CH$_3$CN)$_2$]BF$_4$ while stirring in tetrahydrofuran, in accordance with the method described in a report (K. Mashima, T. Akutagawa, X. Zhang, T. Taketomi, H. Kumobayashi and S. Akutagawa, *J. Organomet. Chem.*, 1992, 428, 213).

The following can be cited as illustrative examples of the iridium complex.

[Ir(L)Cl]$_2$, [Ir(L)Br]$_2$, [Ir(L)I]$_2$,
[Ir(cod)(L)]BF$_4$, [Ir(cod)(L)]ClO$_4$,
[Ir(cod)(L))PF$_6$, [Ir(cod)(L)]BPh$_4$,
[Ir(nbd)(L)]BF$_4$, [Ir(nbd)(L)]ClO$_4$,
[Ir(nod)(L)]PF$_6$, [Ir(nbd)(L)]BPh$_4$ Palladium Complex:

A palladium complex can be prepared by allowing 7,8-dihydro-6H-dibenzo[f,h][1,5]dioxonine-1,13-diyl-bis(diphenylphosphine) to react with π-allylpalladium chloride in accordance with the method described in a report (Y. Uozumi and T. Hayashi, *J. Am. Chem. Soc.*, 1991, 113, 9887).

The following can be cited as illustrative examples of the palladium complex.

PdCl$_2$(L), [(π-allyl)Pd(L)]Cl, (π-allyl)Pd(L)]BF$_4$,
[(π-allyl)Pd(L)]ClO$_4$, [(π-allyl)Pd(L)]PF$_6$,
[(π-allyl)Pd(L)]BPh$_4$ Nickel Complex:

A nickel complex can be prepared, for example, by the method described in "Jikken Kagaku Kouza, Fourth Edition", edited by The Chemical Society of Japan, Vol. 18, Organic Metal Complex, p. 376, 1991, published by Maruzen Publishing, and can also be prepared by dissolving 7,8-dihydro-6H-dibenzo[f,h][1,5]dioxonine-1,13-diyl-bis(diphenylphosphine) and nickel chloride in a mixed solvent of isopropanol and methanol and stirring the solution under heating, in accordance with the method described in a report (Y. Uozumi and T. Hayashi, *J. Am. Chem. Soc.*, 1991, 113, 9887).

The following can be cited as illustrative examples of the nickel catalyst.

NiCl$_2$ (L), NiBr$_2$(L), NiI$_2$(L)

The thus obtained transition metal complexes which contain the novel optically active diphosphine compound as a ligand are useful as a catalyst of asymmetric hydrogenation reaction. When one of these complexes is used as a catalyst, the complex may be used after increasing its purity or directly without purification.

Among these transition metal complexes, particularly a complex which contains ruthenium and an optically active diphosphine compound, 7,8-dihydro-6H-dibenzo[f,h][1,5] dioxonine-1,13-diyl-bis(diphenylphosphine), as a ligand gives higher enantio-selectivity than that of other ruthenium complexes such as of BINAP and p-TolBINAP in the asymmetric hydrogenation reaction of benzoylacetic acid esters.

When asymmetric hydrogenation is carried out using these transition metal complexes, examples of the substrate to be subjected to the asymmetric hydrogenation reaction include carbonyl compounds and unsaturated compounds. Their illustrative examples include α-ketoesters, β-ketoesters and α,β-unsaturated carboxylic acids. More illustratively, methyl benzoylacetate and dehydronaproxen are suitable.

Next, the reaction conditions are described. Since these conditions can vary depending, for example, on the substrate and complex to be used, they cannot be described in a wholesale manner, but the reaction is generally carried out at a temperature of from 10 to 80° C. for a period of from 5 to 24 hours under a hydrogen pressure of from 10 to 60 atmospheres. Amount of the complex to be used is approximately from 1/500 to 1/5,000 (molar ratio) based on the substrate. Any reaction solvent can be used with the proviso that it is stable and does not exert influences upon the substrate and product, and its illustrative examples include lower alcohols such as methanol and ethanol, ethers such as tetrahydrofuran and halogenated hydrocarbons such as methylenechloride and chlorobenzene.

Thus, as has been described in the foregoing, the novel diphosphine compound of the invention is useful particularly as a ligand of a transition metal complex. Also, the transition metal complex is useful as a catalyst of asymmetric hydrogenation reaction. This reaction catalyst is industrially markedly useful, because its use renders possible high yield production of asymmetric hydrides having high optical purity.

EXAMPLES

Examples of the invention are given below by way of illustration and not by way of limitation.

In this connection, the apparatus used in the measurement of physical properties in each example is as follows.

$^1$H NMR: Bruker DRX500 (500 MHz);

$^{31}$P NMR: Bruker DRX500 (202 MHz);

Melting point: Yanaco MP-500D;

Angle of rotation: JASCO Corporation DIP-4;

Gas chromatography: Hewlett Packard 5890-II;

High performance liquid chromatography Hewlett Packard HP1100.

Mass spectrometry Hitachi M-80B.

Example 1a

Synthesis of 3,3'-Dibromo-1,1'-trimethylenedioxydibenzene

In a stream of nitrogen, 100 ml of a dimethylformamide (to be referred to as DMF hereinafter) solution containing 20.03 g (115.8 mmol) of 3-bromophenol was cooled to 5° C. and mixed with 4.9 g (122 mmol) of 60% sodium hydride. After 1 hour of stirring at room temperature, this was mixed with 25 ml of a DMF solution containing 11.5 g (57 mmol) of trimethylene dibromide and stirred at 70° C. for 20 hours. The reaction solution was extracted with 800 ml of ethyl acetate and washed with water (200 ml, 5 times) and saturated brine (100 ml, twice). The organic layer was dried with anhydrous sodium sulfate, and then the solvent was evaporated under a reduced pressure. By purifying the residue by a silica gel column chromatography, 13.70 g (yield 62%) of the title compound was obtained as a colorless oil.

$^1$H-NMR (CDCl$_3$): δ 2.23 (2H, dddd, J=6.1 Hz), 4.11 (4H, t, J=6.1 Hz), 6.83 (2H, ddd, J=8.3, 2.4, 1.1 Hz), 7.06–7.08 (4H, m), 7.12 (2H, t, J=8.3 Hz); EI-MS: m/z 386 (M$^+$).

Example 1b

Synthesis of 1,1'-Trimethylenedioxydibenzene-3,3'-diyl-bis(diphenylphosphine Oxide)

A 1.66 g (68.3 mmol) portion of magnesium pieces were put into a four neck flask, the atmosphere in the reaction contained equipped with a thermometer, a condenser and a pressure equalizer-attached dropping funnel was completely replaced by nitrogen, and then 3 ml of anhydrous tetrahydrofuran (to be referred to as THF hereinafter) was added thereto. While stirring under water-cooling, 60 ml of a THF solution containing 12.01 g (31.1 mmol) of 3,3'-dibromo-1,1'-trimethylenedioxydibenzene was added dropwise to the solution, and the stirring was continued at room temperature for 2 hours. While stirring under water-cooling, 70 ml of a THF solution containing 15.6 g (65.9 mmol) of diphenylphosphinyl chloride was added dropwise to the thus obtained mixed solution, and the stirring was continued at room temperature for 15 hours. The reaction solution was extracted with 40 ml of ethyl acetate and washed with 150 ml of 1 N hydrochloric acid, 150 ml of water and 100 ml of saturated brine in that order. The organic layer was dried with anhydrous sodium sulfate, and then the solvent was evaporated under a reduced pressure. By purifying the residue by a silica gel column chromatography, 16.6 g (yield 80%) of the title compound was obtained as a colorless oil.

$^1$H-NMR (CDCl$_3$): δ (2H, dddd, J=6.1 Hz), 4.11 (4H, t, J=6.1 Hz), 7.05 (2H, d, J=7.5 Hz), 7.12 (2H, dd, J=11.7, 7.5 Hz) 7.28 (2H, d, J=13.3 Hz), 7.34 (2H, dt, J=8.0, 3.8 Hz), 7.43–7.47 (8H, m), 7.52–7.56 (4H, m), 7.63–7.69 (8H, m); $^{31}$P-NMR (CDCl$_3$): δ 30.5; EI-MS: m/z 627 (M−1)$^+$.

Example 1c

Synthesis of (±)-7,8-Dihydro-6H-dibenzo[f,h][1,5]dioxonine-1,13-diyl-bis(diphenylphosphine Oxide)

In a stream of nitrogen, 50 ml of a THF solution containing 3.00 g (4.77 mmol) of 1,1'-trimethylenedioxydibenzene-3,3'-diyl-bis(diphenylphosphine oxide) was cooled to −40° C., and 21 ml of a THF solution containing 0.5 M of lithium diisopropylamide was added dropwise thereto. This reaction solution was added dropwise to a mixture consisting of 2.12 g (13.1 mmol) of ferric chloride, 100 ml of toluene and 100 ml of THF, which was cooled to −40° C., and the resulting mixture was stirred at room temperature for 18 hours. The solvent was evaporated under a reduced pressure, and the residue was dissolved in methylene chloride, washed with 1 N hydrochloric acid, water and saturated brine and then dried with anhydrous magnesium sulfate. After evaporation of the solvent under a reduced pressure, the residue was purified by a silica gel column chromatography to obtain 1.10 g (yield 37%) of the title compound.

mp: 288° C. (decompose); $^1$H-NMR (CDCl$_3$): δ 1.66 (2H, m), 3.99 (2H, dt, J=12.0, 4.4 Hz), 4.07 (2H, dt, J=12.0, 5.6 Hz), 6.84 (2H, ddd, J=13.5, 7.7, 1.0 Hz), 6.86 (2H, d, J=8.1 Hz), 7.07 (2H, dt, J=7.9, 3.3 Hz), 7.12–7.16 (4H, m), 7.23–7.28 (6H, m), 7.30–7.37 (6H, m), 7.63–7.68 (4H, m); $^{31}$P-NMR (CDCl$_3$): δ 29.4; CI-MS: m/z 627 (M+1)$^+$.

Example 1d

Optical Resolution of (±)-7,8-Dihydro-6H-dibenzo[f,h][1,5]dioxonine-1,13-diyl-bis(diphenylphosphine Oxide)

A 23 ml portion of an acetonitrile solution containing 2.77 g (7.36 mmol) of (−)-dibenzoyl-L-tartaric acid was added dropwise to a mixture consisting of 4.60 g (7.34 mmol) of (±)-7,8-dihydro-6H-dibenzo[f,h][1,5]dioxonine-1,13-diyl-bis (diphenylphosphine oxide) and 46 ml of acetonitrile. After 30 minutes of heating under reflux, this was cooled to room temperature and 2.69 g of the thus precipitated solid was collected by filtration. The thus obtained solid was heated under reflux for 10 minutes in 13.5 ml of acetonitrile, and 2.07 g of white solid was collected by filtration. The solid was dissolved in 40 ml of chloroform, mixed with 20 ml of 1 N sodium hydroxide aqueous solution and stirred at room temperature for 1 hour. The organic layer was separated, washed with water and saturated brine in that order and then dried with anhydrous sodium sulfate. By evaporating the solvent under a reduced pressure, 1.31 g of 100% ee (−)-7,8-dihydro-6H-dibenzo[f,h][1,5]dioxonine-1,13-diyl-bis (diphenylphosphine oxide).

$[α]^D{}_{25}$ −174.1° (c=0.506, CHCl$_3$).

Example 1e

Synthesis of (−)-7,8-Dihydro-6H-dibenzo[f,h][1,5]dioxonine-1,13-diyl-bis(diphenylphosphine)

A 2.1 g (16 mmol) portion of trichlorosilane was added dropwise to a mixture of 0.49 g (0.78 mmol) of (−)-7,8-dihydro-6H-dibenzo[f,h][1,5]dioxonine-1,13-diyl-bis (diphenylphosphine oxide), 2.3 g (19 mmol) of dimethylaniline and 20 ml of toluene, and the resulting mixture was stirred at 100° C. for 18 hours. The reaction mixture was ice-cooled, mixed with 15 ml of 4 N sodium hydroxide aqueous solution and stirred at room temperature for 30 minutes. After separation of layers, the water layer was extracted with 50 ml of butyl acetate, and the combined organic layer was washed with 1 N hydrochloric acid (30 ml×2), water (30 ml×2) and 30 ml of saturated brine. After drying with anhydrous magnesium sulfate, the solvent was evaporated under a reduced pressure and the resulting residue was purified by a silica gel column chromatography to obtain 0.45 g (yield 97%) of the title compound as a white solid.

mp: 85° C. $^1$H-NMR (CDCl$_3$): δ 1.78 (2H, m) 4.11 (2H, dt, J=11.7, 4.4 Hz), 4.16 (2H, dt, J=11.7, 5.7 Hz), 6.77 (2H, d, J=7.6 Hz), 6.88 (2H, dd, J=8.0, 1.0 Hz), 7.06–7.11 (4H, m), 7.14–7.20 (8H, m), 7.29–7.32 (6H, m), 7.50–7.54 (4H, m); $^{31}$P-NMR (CDCl$_3$): δ −10.8; CI-MS: m/z 595 (M+1)$^+$; $[α]^D{}_{25}$: 234.2° (c=0.506, CHCl$_3$).

Example 2a

Synthesis of 1,1'-Trimethylenedioxydibenzene-3,3'-diyl-bis(diphenylphosphate)

A 0.65 g (26.7 mmol) portion of magnesium pieces were put into a three neck flask, the atmosphere in the reaction container equipped with a thermometer, a condenser and a pressure equalizer-attached dropping funnel was completely replaced by nitrogen, and then 2 ml of anhydrous THF was added thereto. While stirring under water-cooling, 18 ml of a THF solution containing 4.69 g (12.1 mmol) of 3,3'-dibromo-1,1'-trimethylenedioxydibenzene was added dropwise to the solution, and the stirring was continued at room temperature for 2 hours. The reaction solution was added dropwise to 35 ml of a THF solution containing 6.69 g (25 mmol) of diphenyl chlorophosphate, which was cooled to 5° C., and the stirring was continued at room temperature for 18 hours. The solvent was evaporated under a reduced pressure and the residue was extracted with 200 ml of ethyl acetate and washed with 100 ml of saturated ammonium chloride aqueous solution, 100 ml of water and 100 ml of saturated brine in that order. The organic layer was dried with anhydrous sodium sulfate, and then the solvent was evaporated under a reduced pressure. By purifying the residue by a silica gel column chromatography, 3.33 g (yield 40%) of the title compound was obtained as a colorless oil.

$^1$H-NMR (CDCl$_3$): δ 2.26 (2H, dddd, J=6.1 Hz), 4.17 (4H, t, J=6.1 Hz), 7.11–7.15 (6H, m), 7.16–7.20 (8H, m), 7.26–7.30 (8H, m), 7.40 (2H, dt, J=8.1, 5.9 Hz), 7.48 (2H, d, J=15.8 Hz), 7.54 (2H, dd, J=13.6, 7.4 Hz); $^{31}$P-NMR (CDCl$_3$): δ 12.7; EI-MS m/z 691 (M−1)$^+$.

Example 2b

Synthesis of 1,1'-Trimethylenedioxydibenzene-3,3'-diyl-bis(di(3,5-dimethylphenyl)phosphine Oxide)

In a stream of nitrogen, 3 ml of an ice-cooled THF solution containing 1.00 g (1.44 mmol) of 1,1'-trimethylenedioxydibenzene-3,3'-diyl-bis(diphenyl phosphate) was mixed with 12 ml (12 mmol) of 1 M 3,5-dimethylphenylmagnesium bromide THF solution and stirred at room temperature for 15 hours. This was extracted with 200 ml of ethyl acetate and washed with 50 ml of 1 N hydrochloric acid, 100 ml of water and 100 ml of saturated brine. The organic layer was dried with anhydrous sodium sulfate and the solvent was evaporated under a reduced pressure. By purifying the resulting residue by a silica gel column chromatography, 0.99 g (yield 93%) of the title compound was obtained as a colorless solid.

mp.: 62–65° C.; $^1$H-NMR (CDCl$_3$): δ 2.20 (2H, dddd, J=6.1 Hz), 2.31 (24H, s), 4.12 (4H, t, J=6.1 Hz), 7.04 (2H, d, J=8.3 Hz), 7.11 (2H, dd, J=11.6, 7.6 Hz), 7.14 (4H, bs), 7.25 (4H, bs), 7.28 (4H, bs), 7.29–7.35 (4H, m); $^{31}$P-NMR (CDCl$_3$): δ 30.9; EI-MS m/z 740 (M$^+$)$^+$.

Example 2c

Synthesis of (±)-7,8-Dihydro-6H-dibenzo[f,h][1,5]dioxonine-1,13-diyl-bis(di(3,5-dimethylphenyl)phosphine Oxide)

In a stream of nitrogen, 70 ml of a THF solution containing 4.25 g (5.74 mmol) of 1,1'-trimethylenedioxydibenzene-3,3'-diyl-bis(di(3,5-dimethylphenyl)phosphine oxide) was cooled to −40° C., and 25 ml of a THF solution containing 0.5 M of lithium diisopropylamide was added dropwise thereto. This reaction solution was added dropwise to a mixture consisting of 2.23 g (13.8 mmol) of ferric chloride, 100 ml of toluene and 100 ml of THF, which was cooled to −40° C., and the resulting mixture was stirred at room temperature for 18 hours. The solvent was evaporated under a reduced pressure, and the residue was dissolved in methylene chloride, washed with 1 N hydrochloric acid, water and saturated brine and then dried with anhydrous magnesium sulfate. After evaporation of the solvent under a reduced pressure, the residue was purified by a silica gel column chromatography to obtain 1.21 g (yield 29%) of the title compound.

mp: 135–137° C.; $^1$H-NMR (CDCl$_3$): δ 1.79 (2H, m), 2.14 (12H, s), 2.22 (12H, s), 4.11 (2H, dt, J=11.8, 4.3 Hz), 4.21 (2H, dt, J=11.8, 5.6 Hz), 6.81–6.87 (4H, m), 6.95–7.09 (10H, m), 7.22 (2H, s), 7.25 (2H, s); $^{31}$P-NMR (CDCl$_3$): δ 28.5; Cl-MS m/z 739 (M+1)$^+$.

Example 2d

Optical Resolution of (±)-7,8-Dihydro-6H-dibenzo[f,h][1,5]dioxonine-1,13-diyl-bis (di(3,5-dimethylphenyl)phosphine Oxide)

Using SUMICHIRAL OA-3100 (manufactured by Sumika Chemical Analysis Service, 20 mm×250 mm, eluent: ethanol, flow: 5 ml/min.), optical resolution of (±)-7,8-dihydro-6H-dibenzo[f,h][1,5]dioxonine-1,13-diyl-bis(di(3,5-dimethylphenyl)phosphine oxide) was carried out to obtain 928.4 mg of 100% ee (−)-7,8-dihydro-6H-dibenzo[f,h][1,5]dioxonine-1,13-diyl-bis(di(3,5-dimethylphenyl)phosphine oxide).

$[α]^D_{25}$ 222.8° (c=0.50, CHCl$_3$).

Example 2e

Synthesis of (−)-7,8-Dihydro-6H-dibenzo[f,h][1,5]dioxonine-1,13-diyl-bis(di(3,5-dimethylphenyl)phosphine)

A 3.0 g (22 mmol) portion of trichlorosilane was added dropwise to a mixture of 0.77 g (1.04 mmol) of (−)-7,8-dihydro-6H-dibenzo[f,h][1,5]dioxonine-1,13-diyl-bis (di(3,5-dimethylphenyl)phosphine oxide), 3.1 g (25 mmol) of dimethylaniline and 30 ml of toluene, and the resulting mixture was stirred at 100° C. for 18 hours. The reaction mixture was ice-cooled, mixed with 20 ml of 4 N sodium hydroxide aqueous solution and stirred at room temperature for 30 minutes. The reaction solution was extracted with 100 ml of ethyl acetate and the organic layer was washed with 1 N hydrochloric acid (30 ml×2), water (30 ml×2) and 30 ml of saturated brine. After drying with anhydrous sodium sulfate, the solvent was evaporated under a reduced pressure and the resulting residue was purified by a silica gel column chromatography to obtain 0.60 g (yield 82%) of the title compound as a colorless solid.

mp: 232–234° C.; $^1$H-NMR (CDCl$_3$): δ 1.74 (2H, m), 2.07 (12H, s), 2.21 (12H, s), 4.06–4.14 (4H, m), 6.61 (4H, bs), 6.66–6.70 (4H, m), 6.78 (2H, dd, J=8.1, 1.0 Hz), 6.87 (2H, bs), 7.05 (2H, t, J=7.8 Hz), 7.11 (4H, bs); $^{31}$P-NMR (CDCl$_3$): δ −9.4; EI-MS: m/z 705 (M+1)$^+$; $[α]^D_{25}$: 272.7° (c=0.265, CHCl$_3$).

Example 3a

Synthesis of 1,1'-Trimethylenedioxydibenzene-3,3'-diyl-bis(di(4-methylphenyl)phosphine Oxide)

In a stream of nitrogen, 3 ml of an ice-cooled THF solution containing 1.01 g (1.46 mmol) of 1,1'-trimethylenedioxydibenzene-3,3'-diyl-bis(diphenyl phosphate) was mixed with 14 ml (12 mmol) of 0.85 M 4-methylphenylmagnesium bromide THF solution and stirred at room temperature for 4 hours. This was extracted with 200 ml of ethyl acetate and washed with 50 ml of 1 N hydrochloric acid, 100 ml of water and 100 ml of saturated brine. The organic layer was dried with anhydrous sodium sulfate and the solvent was evaporated under a reduced pressure. By purifying the resulting residue by a silica gel column chromatography, 0.90 g (yield 90%) of the title compound was obtained as a colorless solid.

mp: 55–57° C.; $^1$H-NMR (CDCl$_3$) δ 2.19 (2H, dddd, J=6.1 Hz), 2.39 (12H, s), 4.11 (4H, t, J=6.1 Hz), 7.03 (2H, d, J=8.3 Hz), 7.11 (2H, dd, J=11.7, 7.5 Hz), 7.23–7.34 (12H, m), 7.53 (4H, d, J=8.1 Hz), 7.55 (4H, d, J=8.1 Hz); $^{31}$P-NMR (CDCl$_3$): δ 30.5; EI-MS m/z 684 (M+)$^+$.

Example 3b

Synthesis of (±)-7,8-Dihydro-6H-dibenzo[f,h][1,5]dioxonine-1,13-diyl-bis(di(4-methylphenyl)phosphine Oxide)

In a stream of nitrogen, 80 ml of a THF solution containing 4.26 g (6.22 mmol) of 1,1'-trimethylenedioxydibenzene- 3,3'-diyl-bis(di(4-methylphenyl)phosphine Oxide) was cooled to −40° C., and 28 ml of a THF solution containing 0.5 M of lithium diisopropylamide was added dropwise thereto. This reaction solution was added dropwise to a mixture consisting of 2.42 g (14.9mmol) of ferric chloride, 100 ml of toluene and 100 ml of THF, which was cooled to −40° C., and the resulting mixture was stirred at room temperature for 18 hours. The solvent was evaporated under a reduced pressure, and the residue was dissolved in methylene chloride, washed with 1 N hydrochloric acid, water and saturated brine and then dried with anhydrous magnesium sulfate. After evaporation of the solvent under a reduced pressure, the residue was purified by a silica gel column chromatography to obtain 1.03 g (yield 24%) of the title compound.

mp: 138–140° C.; $^1$H-NMR (CDCl$_3$): δ 1.72 (2H, m), 2.30 (6H, s), 2.32 (6H, s), 4.08 (2H, dt, J=11.8, 4.4 Hz), 4.15 (2H, dt, J=11.8, 5.7 Hz), 6.90 (2H, dd, J=13.5, 7.5 Hz), 6.96 (2H, d, J=8.0 Hz), 7.00–7.17 (10H, m), 7.27–7.32 (4H, m), 7.57–7.62 (4H, m); $^{31}$P-NMR (CDCl$_3$): δ 29.7; CI-MS m/z 683 (M+1)$^+$.

Example 3c

Optical Resolution of (±)-7,8-Dihydro-6H-dibenzo [f,h][1,5]dioxonine-1,13-diyl-bis (di(4-methylphenyl)phosphine Oxide)

Using SUMICHIRAL OA-3100 (20 mm$_{33}$ 250 mm, eluent: 2-propanol/methanol=60/40 (by volume), flow: 4.8 ml/min.), optical resolution of (±)-7,8-dihydro-6H-dibenzo [f,h][1,5]dioxonine-1,13-diyl-bis (di(4-methylphenyl) phosphine Oxide) was carried out to obtain 1.01 g of 100% ee (−)-7,8-dihydro-6H-dibenzo[f,h][1,5]dioxonine-1,13-diyl-bis (di(4-methylphenyl)phosphine Oxide).

$[α]^D_{25}$ 154.5° (c=0.52, CHCl$_3$).

Example 3d

Synthesis of (−)-7,8-Dihydro-6H-dibenzo[f,h][1,5] dioxonine-1,13-diyl-bis(di(4-methylphenyl) phosphine)

A 1.6 g (11.9 mmol) portion of trichlorosilane was added dropwise to a mixture of 0.80 g (1.17 mmol) of (−)-7,8-dihydro-6H-dibenzo[f,h][1,5]dioxonine-1,13-diyl-bis (di(4-methylphenyl)phosphine Oxide), 1.72 g (14.2 mmol) of dimethylaniline and 30 ml of toluene, and the resulting mixture was stirred at 100° C. for 18 hours. The reaction mixture was ice-cooled, mixed with 15 ml of 4 N sodium hydroxide aqueous solution and stirred at room temperature for 30 minutes. The reaction solution was extracted with 100 ml of ethyl acetate and the organic layer was washed with 1 N hydrochloric acid (30 ml×2), water (30 ml×2) and 30 ml of saturated brine. After drying with anhydrous sodium sulfate, the solvent was evaporated under a reduced pressure and the resulting residue was purified by a silica gel column chromatography to obtain 0.65 g (yield 85%) of the title compound as a colorless solid.

mp: 108–110° C.; $^1$H-NMR (CDCl$_3$): δ 1.78 (2H, m), 2.26 (6H, s), 2.33 (6H, s), 4.12 (2H, dt, J=11.7, 4.4 Hz), 4.17 (2H, dt, J=11.7, 5.7 Hz), 6.79 (2H, d, J=7.7 Hz), 6.88 (2H, d, J=8.0 Hz), 6.96 (8H, t, J=2.3 Hz), 7.11 (4H, d, J=7.7 Hz), 7.14 (2H, t, J=7.8 Hz), 7.39–7.43 (4H, m); $^{31}$P-NMR (CDCl$_3$) δ −12.7; CI-MS: m/z 651 (M +I)$^+$; $[α]^D_{25}$: 244.1° (c=0.495, CHCl$_3$).

Example 4

Preparation of [RuI(p-cymene)(L1)]I (L1=(−)-7,8-Dihydro-6H-dibenzo[f,h][1,5]dioxonine- 1,13-diyl-bis(diphenylphosphine))

A mixture consisting of [Ru(p-cymene)I$_2$]$_2$ (123.4 mg, 0.126 mol), 150.1 mg (0.250 mmol) of (−)-7,8-dihydro-6H-dibenzo[f,h][1,5]dioxonine-1,13-diyl-bis (diphenylphosphine), 5 ml of methylene chloride and 5 ml of ethanol was stirred at 50° C. for 3 hours in a 20 ml Schlenk tube. After evaporation of the solvent under a reduced pressure, the residue was dried in vacuo to obtain 273.5 mg of the title compound.

$^{31}$P-NMR (CDCl$_3$) δ 43.0 (d, J 62.2 Hz), 26.3 (d, J=62.2 Hz).

Example 5

Preparation of [RuI(p-cymene)(L2)]I (L2=(−)-7,8-Dihydro-6H-dibenzo[f,h][1,5]dioxonine-1,13-diyl-bis(di(3,5-dimethylphenyl)phosphine))

A mixture consisting of [Ru(p-cymene)I$_2$]$_2$ (49 mg, 0.05 mmol), 71 mg (0.1 mmol) of (−)-7,8-dihydro-6H-dibenzo [f,h][1,5]dioxonine-1,13-diyl-bis (di(3,5-dimethylphenyl) phosphine), 4 ml of methylene chloride and 4 ml of ethanol was stirred at 50° C. for 3 hours in 20 ml Schlenk tube. After evaporation of the solvent under a reduced pressure, the residue was dried in vacuo to obtain 120 mg of the title compound.

$^{31}$P-NMR (CDCl$_3$): δ 42.8 (d, J=62.2 Hz), 25.7 (d, J=62.2 Hz).

Example 6

Preparation of [Rh(cod) (L3)]BF$_4$ (L3=(−)-7,8-Dihydro-6H-dibenzo[f,h][1,5]dioxonine-1,13-diyl-bis(di(4-methylphenyl)phosphine))

A mixture consisting of [Rh(cod)$_2$]BF$_4$ (23.0 mg, 0.057mmol), 37.1 mg (0.057 mmol) of (−)-7,8-dihydro-6H-dibenzo[f,h][1,5]dioxonine-1,13-diyl-bis (di(4-methylphenyl)phosphine), 4 ml of methylene chloride and 4 ml of THF was stirred at room temperature for 15 hours in a 20 ml Schlenk tube. After evaporation of the solvent under a reduced pressure, the residue was dried in vacuo to obtain 54.1 mg of the title compound.

$^{31}$P-NMR (CDCl$_3$): δ 24.3 (s), 25.0 (s).

Example 7

Preparation of [Ru (OAc)$_2$(L1)] (L1=(−)-7,8-Dihydro-6H-dibenzo[f,h][1,5]dioxonine-1,13-diyl-bis(diphenylphosphine))

In a stream of nitrogen, a mixture consisting of [Ru(cod) Cl$_2$]$_n$ (46.8 mg, 0.167 mmol), 99.8 mg (0.168 mmol) of (−)-7,8-dihydro-6H-dibenzo[f,h][1,5]dioxonine-1,13-diyl-bis(diphenylphosphine), 0.25 ml (1.79 mmol) of triethylamine and 8 ml of toluene was heated under reflux for 15 hours in a 20 ml Schlenk tube. After evaporation of the solvent under a reduced pressure, 27.6 mg (0.336 mmol) of sodium acetate and 8 ml of t-butanol were put into the tube and the mixture was heated under reflux for 18 hours. After evaporation of the solvent under a reduced pressure, the residue was dried in vacuo to obtain 135.9 mg of the title compound.

$^{31}$P-NMR (CDCl$_3$): δ 65.7 (s).

Example 8

Preparation of [Ru(OAc)$_2$(L2)] (L2=(−)-7,8-Dihydro-6H-dibenzo[f,h][1,5]dioxonine-1,13-diyl-bis(di(3,5-dimethylphenyl)phosphine))

In a stream of nitrogen, a mixture consisting of [Ru(cod) Cl$_2$]$_n$ (51.8 mg, 0.185 mmol), 130.8 mg (0.185 mmol) of (−)-7,8-dihydro-6H-dibenzo[f,h][1,5]dioxonine-1,13-diyl-bis (diphenylphosphine), 0.25 ml (1.79 9mmol) of triethylamine and 8 ml of toluene was heated under reflux for 15 hours in a 20 ml Schlenk tube. After evaporation of the solvent under a reduced pressure, 30.4 mg (0.37 mmol) of sodium acetate and 8 ml of t-butanol were put into the tube and the mixture was heated under reflux for 18 hours. After evaporation of the solvent under a reduced pressure, the residue was dried in vacuo to obtain 171.3 mg of the title compound.

31P-NMR (CDCl$_3$): δ 65.2 (s).

Application Example 1

Asymmetric Hydrogenation of Methyl Benzoylacetate

In a stream of nitrogen, a mixture consisting of 46.8 mg of (Ru(cod)Cl$_2$)$_n$ (a polymer form), 99.8 mg (0.168 mmol) of (−)-7,8-dihydro-6H-dibenzo[f,h][1,5]dioxonine-1,13-diyl-bis (diphenylphosphine), 0.25 ml (1.79 mmol) of triethylamine and 8 ml of toluene was heated under reflux for 15 hours. After evaporation of the solvent under a reduced pressure, the residue was dried in vacuo.

A 2.3 mg (0.0014 mmol) portion of the thus obtained complex, 0.5 g (2.8 mmol) of methyl benzoylacetate and 2 ml of methanol were put into a stainless steel autoclave and stirred at 50° C. for 14 hours under a hydrogen pressure of 30 atm to obtain optically active methyl 3-phenyl-3-hydroxypropionate. When measured by HPLC, the conversion ratio was 100% and its optical purity was 96.5% ee.

Measurement of conversion ratio and % ee; CHIRALCEL OD (4.6 mnn × 250 mm); Eluent: hexane/2-propanol=95/5 (by volume); Flow rate: 1.0 ml/min. Detection: 254 nm.

Application Example 2

Asymmetric Hydrogenation of Dehydronaproxen

A 3.6 mg (0.0044 mmol) portion of the complex obtained in Example 7, 1.0 g (4.4 mmol) of dehydronaproxen and 6 ml of methanol were put into a stainless steel autoclave and stirred at 15° C. for 10 hours under a hydrogen pressure of 50 atm to obtain optically active naproxen. When measured by HPLC, the conversion ratio was 99% or more and its optical purity was 89.2% ee.

Measurement of conversion ratio and % ee; CHIRAL AGP (4.0 mm×100 mm); Eluent: 60 mM phosphate buffer; Flow rate: 0.3 ml/min. Detection: 265 nm.

Application Example 3

Asymmetric Hydrogenation of Dehydronaproxen

The complex obtained in Example 8 (4.1 mg, 0.0044 mmol), dehydronaproxen (1.0 g, 4.4 mmol) and 6 ml of methanol were put into a stainless steel autoclave and stirred at 15° C. for 15 hours under a hydrogen pressure of 50 atm to obtain optically active naproxen. When measured by HPLC, the conversion ratio was 99% or more and its optical purity was 93.5% ee.

In this case, the measurement of conversion ratio and % ee was carried out by the same method of Application Example 2.

Comparative Example 1

Optically active methyl 3-phenyl-3-hydroxypropionate was obtained by carrying out asymmetric hydrogenation of methyl benzoylacetate in the same manner as described in Application Example 1, except that the ruthenium complex was changed to Ru$_2$Cl$_4$[(R)-p-TolBINAP]$_2$NEt$_3$. The conversion ratio was 93.1% and its optical purity was 87.0% ee.

Comparative Example 2

Optically active naproxen was obtained by carrying out asymmetric hydrogenation of dehydronaproxen in the same manner as described in Application Example 2, except that the ruthenium complex was changed to [RuCl(p-cymene)(R)-SEGPHOS]Cl. The conversion ratio was 99% or more and its optical purity was 87.0% ee.

What is claimed is:

1. A diphosphine compound represented by a formula (1):

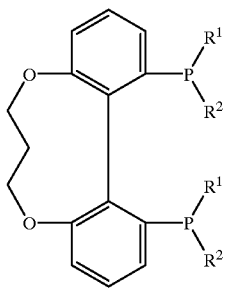

(1)

wherein $R^1$ and $R^2$ each independently represents a cycloalkyl group, an unsubstituted or substituted phenyl group or a five-membered aromatic heterocyclic group.

2. A diphosphine oxide compound represented by a formula (2):

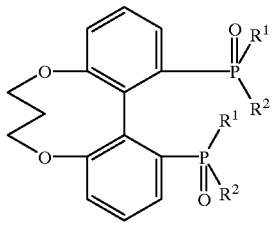

(2)

wherein $R^1$ and $R^2$ each independently represents a cycloalkyl group, an unsubstituted or substituted phenyl group or a five-membered aromatic heterocyclic group.

3. A diphosphine oxide compound represented by a formula (3):

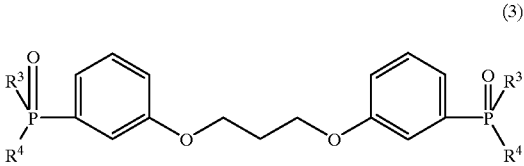

(3)

wherein $R^3$ and $R^4$ each independently represents a cycloalkyl group, an unsubstituted or substituted phenyl group, a five-membered aromatic heterocyclic group, a lower alkoxyl group, phenoxy group, benzyloxy group, chlorine atom or bromine atom.

4. A transition metal complex selected from the group consisting of rhodium complexes, ruthenium complexes, iridium complexes, palladium complexes and nickel complexes, which contains an optically active compound of the compound of claim 1, as a ligand.

5. A catalyst which contains a transition metal complex represented by a formula (4):

$$M_mL_nX_pS_q \tag{4}$$

wherein M represents a transition metal selected from the group consisting of rhodium, ruthenium, iridium, palladium and nickel, L represents an optically active diphosphine compound of the compound of claim 1, X is selected from the group consisting of Cl, Br, I, acetoxy group, methallyl group and π-allyl group, S represents $NEt_3$, Et represents ethyl group, m is 1 or 2, n is 1 or 2, p is 2 or 4 and q is 0 or 1, with the proviso that (i) when M=Rh, then X=Cl, Br or I, m=2, n=2, p=2 and q=0, (ii) when M=Ru and X=acetoxy group, then m=1, n=1, p=2 and q=0, (iii) when M=Ru and X=Cl or Br, then m=2, n=2, p=4 and q=1, or (iv) when M=Ru and X=methallyl, then m=1, n=1, p=2 and q=0, (v) when M=Ir, then X=Cl, Br or I, m=2, n=2, p=2 and q=0, (vi) when M=Pd and X=Cl, Br or I, then m=1, n=1, p=2 and q=0, (vii) when M=Pd and X=π-allyl, then m=2, n=2, p=2 and q=0, and (viii) when M=Ni, then X=Cl, Br or I, m=1, n=1, p=2 and q=0.

6. A catalyst which contains a transition metal complex represented by a formula (5):

$$[M_mX_pL_nZ_q]Y_r \tag{5}$$

wherein M represents a transition metal selected from the group consisting of rhodium, ruthenium, iridium and palladium, L represents an optically active diphosphine compound of the compound of claim 1, X represents 1,5-cyclooctadiene, norbornadiene, Cl, Br or I, Z represents benzene or paracymene, Y represent $BF_4$, $ClO_4$, $PF_6$, $BPh_4$, Cl, Br or I and Ph represent phenyl group, m is 1, n is 1, p is 0, 1 or 2, q is 0 or 1 and r is 0, 1 or 2, with the proviso that (i) when M=Rh, then X=cod or nbd, Y=$BF_4$, $ClO_4$, $PF_6$ or $BPh_4$, m=1, n=1, p=1, r=1 and q=0, (ii) when M=Ru and Y=Cl, Br or I, then X=Cl, Br or I, Z=benzene or paracymene, m=1, n=1, p=1, q=1 and r=1, (iii) when M=Ru and Y=$BF_4$, $ClO_4$, $PF_6$ or $BPh_4$, then m=1, n=1, p=0, q=0 and r=2, (iv) when M=Ir, then X=cod or nbd, Y=$BF_4$, $ClO_4$, $PF_6$ or $BPh_4$, m=1, n=1, r=1, p=1 and q=0, (v) when M=Pd, then Y=$BF_4$, $ClO_4$, $PF_6$ or $BPh_4$, m=1, n=1, r=1, p=0 and q=0, and (vi) when M=Ni, then X=Cl, Br or I, then m=1, n=1, p=2, q=0 and r=0, wherein cod represents 1,5-cyclooctadiene and nbd represents norbornadiene.

7. An asymmetric hydrogenation catalyst which contains the transition metal complex of claim 4.

* * * * *